(12) United States Patent
Yu

(10) Patent No.: US 10,258,482 B1
(45) Date of Patent: Apr. 16, 2019

(54) ARTIFICIAL INTERVERTEBRAL IMPLANT

(71) Applicant: Kidong Yu, Piscataway, NJ (US)

(72) Inventor: Kidong Yu, Piscataway, NJ (US)

(73) Assignee: UKI LLC, Bellevue, WA (US)

( * ) Notice: Subject to any disclaimer, the term of this patent is extended or adjusted under 35 U.S.C. 154(b) by 0 days.

(21) Appl. No.: 15/805,353

(22) Filed: Nov. 7, 2017

(51) Int. Cl.
*A61F 2/44* (2006.01)
*A61F 2/46* (2006.01)
*A61F 2/30* (2006.01)

(52) U.S. Cl.
CPC ........ *A61F 2/4425* (2013.01); *A61F 2/30771* (2013.01); *A61F 2/4611* (2013.01); *A61F 2002/30004* (2013.01); *A61F 2002/30476* (2013.01); *A61F 2220/0025* (2013.01); *A61F 2310/00023* (2013.01); *A61F 2310/00029* (2013.01); *A61F 2310/00059* (2013.01)

(58) Field of Classification Search
CPC ...... A61F 2/4611; A61F 2/442; A61F 2/4425; A61F 2002/4435; A61F 2002/444; A61F 2002/443
USPC ...................... 606/246–249; 623/17.11–17.16
See application file for complete search history.

(56) References Cited

U.S. PATENT DOCUMENTS

| | | | |
|---|---|---|---|
| 7,563,286 B2 * | 7/2009 | Gerber | A61F 2/441 623/17.14 |
| 8,092,542 B2 | 1/2012 | Bryan | |
| 8,167,948 B2 | 5/2012 | Paul | |
| 8,377,138 B2 | 2/2013 | Reo | |
| 8,591,586 B2 | 11/2013 | Link | |
| 8,679,181 B2 | 3/2014 | Bechmann | |
| 8,858,635 B2 | 10/2014 | Hovorka | |
| 8,864,832 B2 | 10/2014 | Carls | |
| 9,084,681 B2 | 7/2015 | Berger | |
| 2016/0250035 A1 * | 9/2016 | de Villiers | A61F 2/442 623/17.15 |

* cited by examiner

*Primary Examiner* — Julianna N Harvey
*Assistant Examiner* — Christina Negrellirodriguez
(74) *Attorney, Agent, or Firm* — John H. Choi & Associates LLC

(57) ABSTRACT

An intervertebral implant comprising a core member operably coupled between an upper base member and a lower base member, and a core spacer positioned within an inner cavity of the core member. An outer cavity extends between the core member upper end and lower end, and radially between the inner cavity and an outer surface of the core member. A core member inner wall is formed between the inner cavity and the outer cavity, and a core member outer wall is formed between the outer cavity and the outer surface of the core member. At least one first locking member is positioned on at least one of the core member upper end and the core member lower end and at least one second locking member is positioned on an inner surface of at least one of the upper base member and the lower base member for locking engagement.

19 Claims, 16 Drawing Sheets

ARTIFICIAL INTERVERTEBRAL IMPLANT

FIELD

The present disclosure relates to surgical implants and in particular to artificial intervertebral disc replacement implants.

BACKGROUND

Total disc replacement involves surgically replacing an intervertebral disc with an artificial implant to treat degenerative disc disease and stenosis on the cervical, thoracic, or lumbar spine.

There are various artificial discs in the prior art. The artificial discs in the prior art could be categorized in three general types: mechanical, composite, and elastic.

Mechanical discs comprise two base plates pivotally coupled by, for example, a ball and socket. An example of a mechanical disc is a product manufactured by MEDTRONIC and sold as "PRESTIGE." One disadvantage to mechanical discs is that they do not provide sufficient shock absorption. Another disadvantage is that they create a lot of friction and wear, including the creation of debris.

Composite discs comprise of base plates pivotally coupled by a polymer core. Examples of composite discs include DEPUY SYNTHES' "PRODISC-C," MEDTRONIC'S "BRYAN," NUVASIVE'S "PCM," GLOBUS MEDICAL'S "SECURE-C," and ZIMMER BIOMET'S "MOBI-C." These products provide some shock absorption but do not cure the deficiencies of friction or wear. Furthermore, both mechanical and composite discs have cores that can separate, increasingly the likelihood of injury. Thus, composite discs in the prior art are susceptible to failure and potential injury.

U.S. Pat. No. 8,679,181 discloses DEPUY SYNTHES' "PRODISC-C" composite disc, which comprises a lower base coupled to a convex inner surface and an upper base coupled to a concave inner surface. The joint formed by the convex and concave surfaces more freely articulates and therefore are more likely to dislocate. Thus, the movement of the joint or bearing surfaces creates stress concentration and causes friction, thereby creating debris.

U.S. Pat. No. 8,092,542 discloses MEDTRONIC'S "BRYAN" composite disc, which comprises a polymer core between two concave base plates. When one side of the disc is compressed, the polymer core is displaced in an opposing direction. However, much friction is caused and the friction between the polymer core and the base plates can cause wear and create debris, which could be hazardous to the human body.

U.S. Pat. No. 8,591,586 discloses NUVASIVE'S "PCM" composite disc, which operates similarly to MEDTRONIC'S "BRYAN" and suffers from the same disadvantages.

U.S. Pat. No. 8,167,948 discloses GLOBUS MEDICAL'S "SECURE-C" composite disc, which allows the polymer core between the two concave base plates to move within a predefined range to allow for translational motion. While allowing for translational motion, it still suffers from the other disadvantages of the prior art mentioned above.

U.S. Pat. No. 8,858,635 discloses ZIMMER BIOMET'S "MOBI-C" composite disc, which features large indentations on the polymer core matched to smaller protrusions on the base plates. The protrusions limit movement of the core to the range allowed for by the indentations. While this might provide a safeguard against separation, it also introduces another point of friction between the core and the protrusion. In addition, the superior base member is still free from the core, which may cause dislocation.

Elastic discs in the prior art usually comprise of a rubber core between the base plates. An example of an elastic disc is disclosed by U.S. Pat. No. 8,377,138 and manufactured by SPINAL KINETICS as "M6-C." It comprises a compressible core encased in fibrous material. Although this product provides improved shock absorption and mechanical resistance to prevent dislocation during motion, the product is more difficult and costlier to manufacture due to the complexity of the components.

Another artificial disc in the prior art is U.S. Pat. No. 9,084,681, which discloses an intervertebral implant with a core comprising a bag filled with beads. This would provide increased shock absorption but the lack of structural support increases the likelihood of failure.

In the prior art, the base plates, or endplates, are commonly made from titanium alloy or cobalt chromium with a porous finish or porous coating to allow fusing with the natural bone. Protrusions on the base plates provide traction and prevent the disc from sliding.

The cores of the elastic or composite discs are typically made from a radiolucent polymer. This is problematic because it prevents clear x-ray imagery of the core for a surgeon to evaluate intraoperatively whether the implant is properly sized and positioned.

Intervertebral discs can be implanted anteriorly or posteriorly. When implanted posteriorly, access is restricted by surrounding nerves and requires a narrower implant. U.S. Pat. No. 8,864,832 discloses an intervertebral implant for posterior implantation. The implant comprises a ball and socket between two narrow base plates. However, this device exhibits all the disadvantages of similar devices for anterior implantation.

As seen above, typical failure of disc implants include dislocation of joints, device migration, subsidence and wear debris. Typical causes of failure come from the device components becoming loosened and the failure to support the load required especially due to lordosis—the difference between the anterior and posterior height.

Therefore, a need exists for an artificial intervertebral disc that solves the problems in the prior art and that is low-friction, wear-resistant, shock-absorbent, debris-free, and provides stability in all directions that is implantable anteriorly and posteriorly.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The artificial intervertebral disc of the present invention solves the problems of the prior art and provides additional advantages.

In general, the artificial intervertebral disc of the present invention comprises a substantially cylindrical core member, a core spacer, an upper base, and a lower base. The core member has an inner cavity at its center surrounded by an inner wall, an outer cavity outside the inner wall, and an outer wall surrounding the outer cavity. The core spacer is located within the inner cavity. The upper and lower bases are coupled to opposing ends of the core member.

More specifically, in one aspect, the present invention provides an intervertebral implant comprising: a substantially cylindrical core member having an upper end and an axially opposing lower end, the core member comprising: an inner cavity extending axially between a center of the upper end and a center of the lower end, and at least one outer cavity extending axially between the first upper and the lower end, and radially between the inner cavity and a radially outer surface of the core member, a core member inner wall formed between the inner cavity and the at least one outer cavity, a core member outer wall formed between the at least one outer cavity and the outer surface of the core member, the core member outer wall having an upper radial extension positioned on the upper end of core member, a lower radial extension positioned on the lower end of the core member, and an axial extension positioned therebetween, and at least one first locking member positioned on at least one of the core member upper end and the core member lower end; a core spacer positioned within the inner cavity; an upper base member positioned on the upper end of the core member, the upper base member having an upper retaining wall positioned on a periphery thereof, the upper retaining wall having an upper groove positioned on an inner portion thereof; a lower base member positioned on the lower end of the core member, the lower base member having a lower retaining wall positioned on a periphery thereof, the lower retaining wall having a lower groove positioned on an inner portion thereof; and at least one second locking member positioned on an inner surface of at least one of the upper base member and the lower base member; wherein the upper and lower base members are operably coupled with the core member by engagement of the upper radial extension and the upper groove, and the lower radial extension and the lower groove, and by engagement of the at least one first locking member and the at least one second locking member.

In another aspect, the present invention provides an intervertebral implant comprising: a substantially cylindrical core member having an upper end and an opposing lower end, the core member comprising: an inner cavity extending axially between a center of the upper end and a center of the lower end, and at least one outer cavity extending axially between the upper end and the lower end, and radially between the inner cavity and an outer surface of the core member, a core member inner wall formed between the inner cavity and the at least one outer cavity, and a core member outer wall formed between the at least one outer cavity and the outer surface of the core member, the core member outer wall having an upper radial extension positioned on the upper end of core member, a lower radial extension positioned on the lower end of the core member, and an axial extension positioned therebetween; a core spacer positioned within the inner cavity; an upper base member positioned on the upper end of the core member, the upper base member having an upper retaining wall positioned on a periphery thereof, the upper retaining wall having an upper groove positioned on an inner portion thereof; a lower base member positioned on the lower end of the core member, the lower base member having a lower retaining wall positioned on a periphery thereof, the lower retaining wall having a lower groove positioned on an inner portion thereof; wherein the upper and lower base members are operably coupled with the core member by engagement of the upper radial extension and the upper groove, and the lower radial extension and the lower groove.

In yet another aspect, the present invention provides an intervertebral implant comprising: a core member having an upper end and an opposing lower end, the core member comprising: an inner cavity extending axially between a center of the upper end and a center of the lower end, and at least one outer cavity extending axially between the upper end and the lower end, and radially between the inner cavity and an outer surface of the core member, a core member inner wall formed between the inner cavity and the at least one outer cavity, and a core member outer wall formed between the at least one outer cavity and the outer surface of the core member; at least one first locking member positioned on at least one of the core member upper end and the core member lower end; and a core spacer positioned within the inner cavity.

BRIEF DESCRIPTION OF DRAWINGS

The foregoing summary, as well as the following detailed description of presently preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

Figure 1:
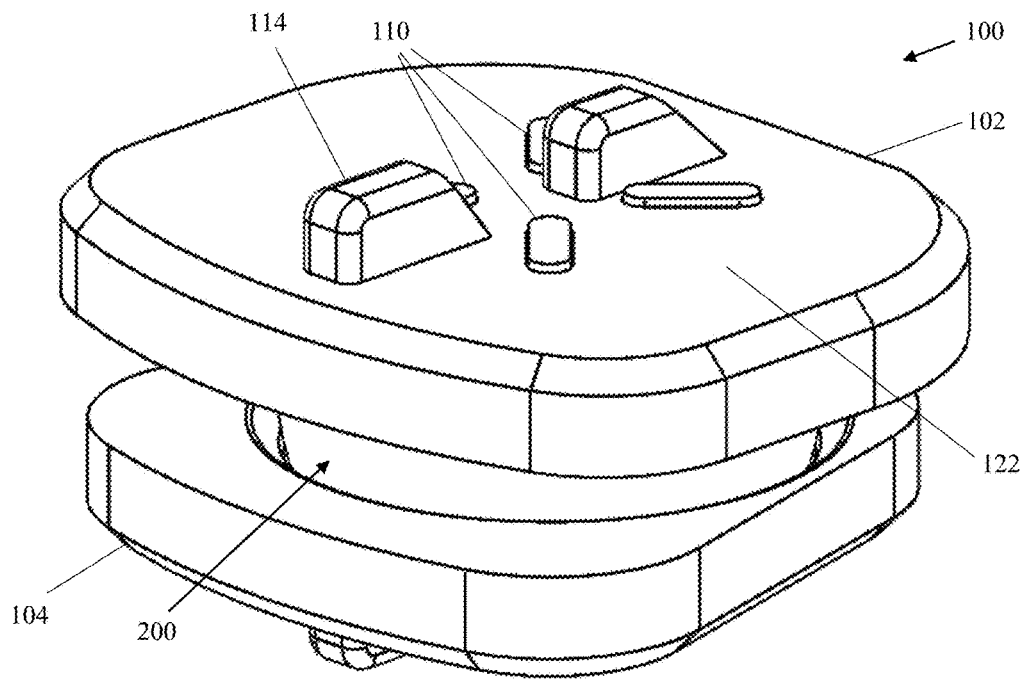
FIG. 1 is a perspective view of an embodiment of an artificial intervertebral disc of the present invention.
Figure 2:
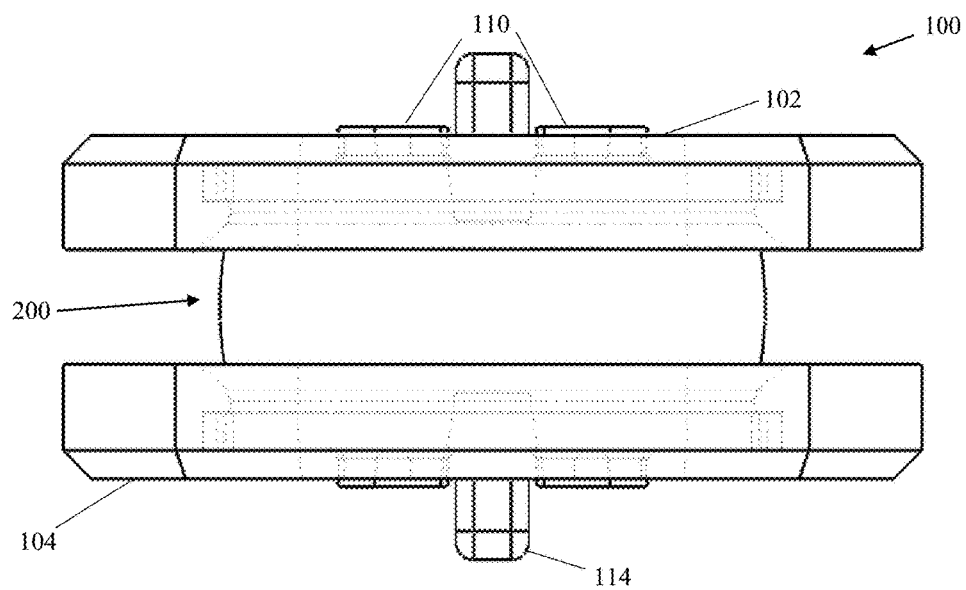
FIG. 2 is a side view of the artificial intervertebral disc of FIG. 1 with a cross-sectional view superimposed therewithin.
Figure 3:
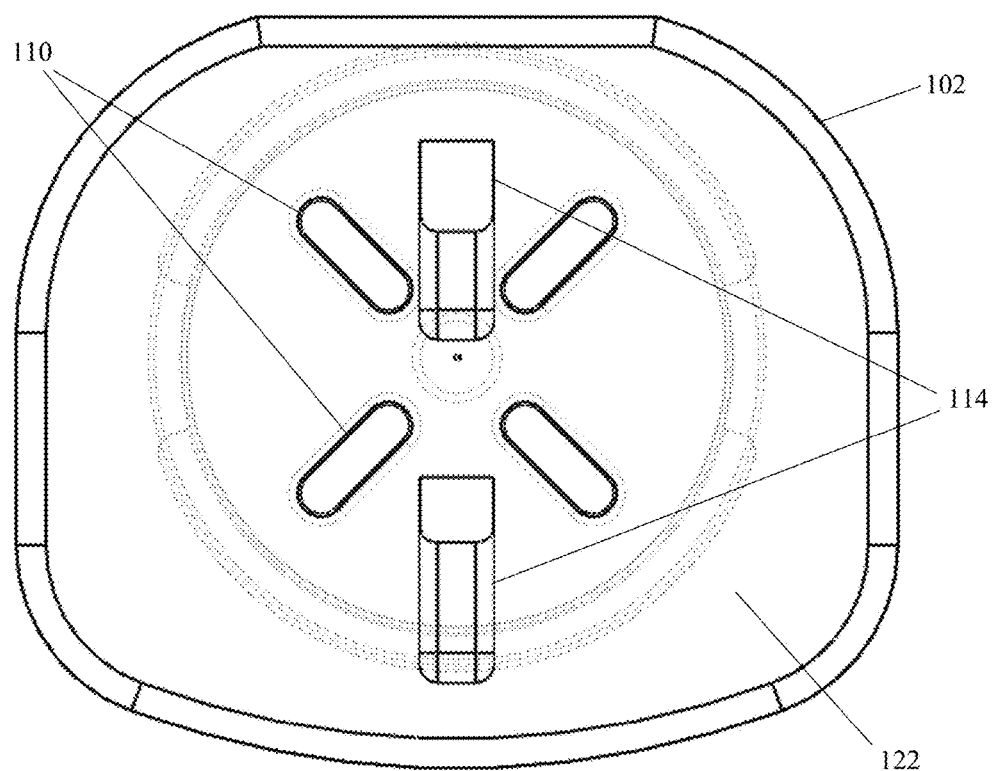
FIG. 3 is a top view of the artificial intervertebral disc of FIG. 1 with a cross-sectional view superimposed therewithin.
Figure 4:
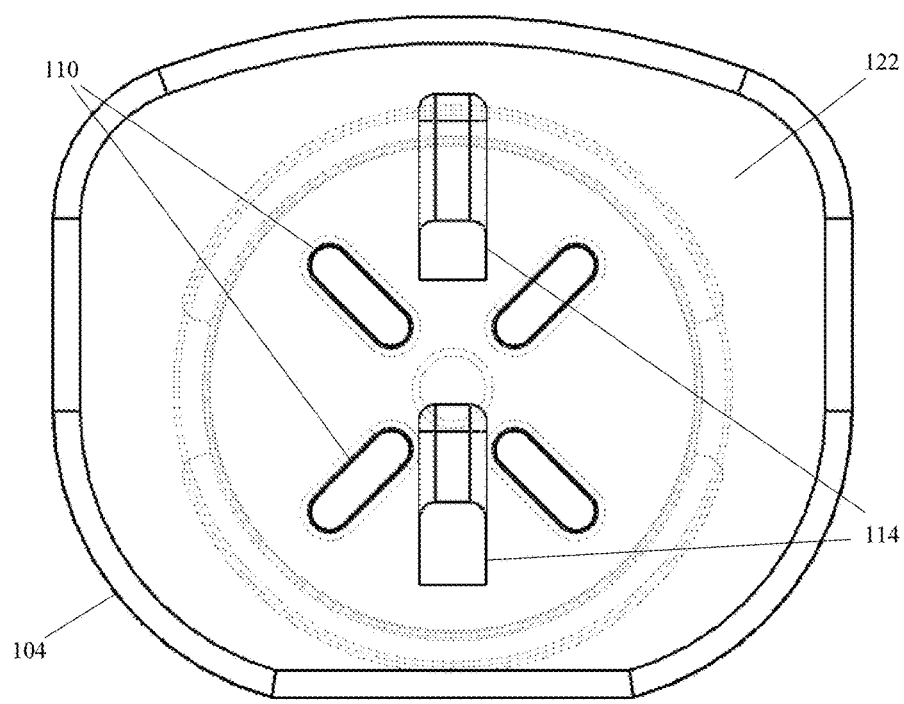
FIG. 4 is a bottom view of the artificial intervertebral disc of FIG. 1 with a cross-sectional view superimposed therewithin.

To facilitate an understanding of the invention, identical reference numerals have been used, when appropriate, to designate the same or similar elements that are common to the figures. Further, unless stated otherwise, the features shown in the figures are not drawn to scale, but are shown for illustrative purposes only.

DETAILED DESCRIPTION

Certain terminology is used in the following description for convenience only and is not limiting. The article "a" is intended to include one or more items, and where only one item is intended the term "one" or similar language is used. Additionally, to assist in the description of the present invention, words such as top, bottom, side, upper, lower, front, rear, inner, outer, right and left are used to describe the accompanying figures. The terminology includes the words above specifically mentioned, derivatives thereof, and words of similar import.

Referring to FIGS. 1-13, the exemplar embodiments of the intervertebral disc 100, 101 comprise a cylindrical core member 200, a superior base or an upper base member 102 positioned on an upper end 230 of the core member 200, and an inferior base or a lower base member 104 positioned on an opposing lower end 232 of the core member 200.

Figure 9:
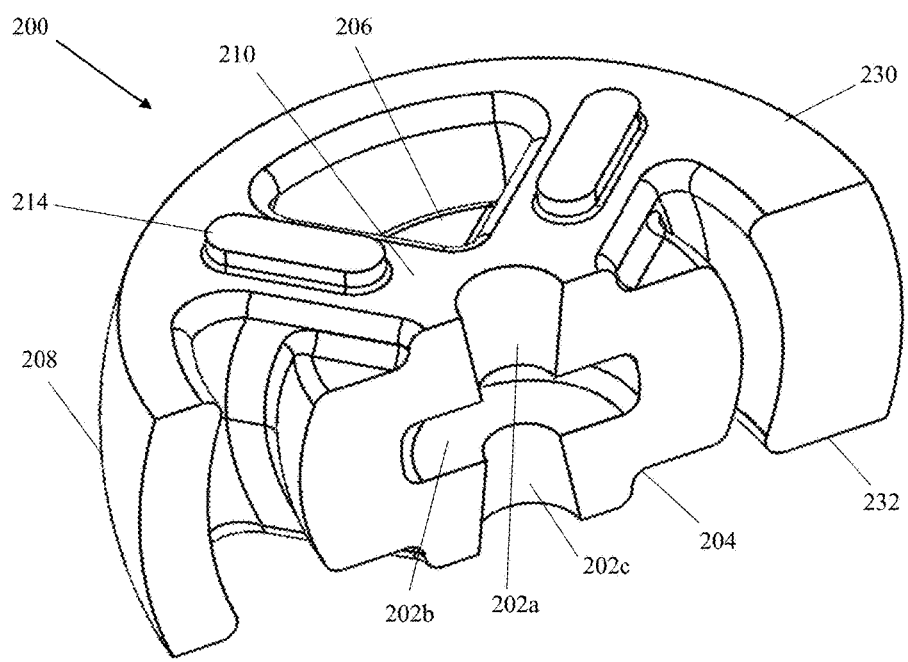
FIG. 9 is a partial cross-sectional perspective view of the core member of the embodiments of the artificial intervertebral disc of the present invention.

Referring to FIGS. 5-11, the core member 200 comprises an inner cavity 202 extending axially between the upper end 230 and the lower end 232 of the core member 200. As shown in FIG. 9, the inner cavity 202 includes an upper section 202a, an intermediate section 202b and a lower section 202c, and extends through the core member 200. In the present embodiments, the upper and lower sections 202a, 202c are tapered from the upper and lower ends 230, 232, respectively, toward the intermediate section 202b. The intermediate section 202b has a width that is greater than the upper and lower sections 202a, 202b, and is sized and shaped to receive a core spacer 220, which is described in more detail below. An inner wall 204 is formed around the inner cavity 202.

Still referring to FIGS. 5-11, at least one outer cavity 206 is formed adjacent to and radially outward from the inner wall 204. In the exemplar embodiment, the core member 200 includes four outer cavities 206 substantially aligned with a circumference of the core member 200 and substantially uniformly spaced apart. The outer cavities 206 are separated by four radial walls 210 which extend axially between the upper and lower ends 230, 232 of the core member 200 and radially between the inner cavity 202 and an outer wall 208 of the core member 200. The outer cavities 206 widen at the upper and lower ends 230, 232 and are tapered therebetween, as shown for example in FIGS. 9 and 10. The radial walls 210 provide both axial and torsional stability, while the outer cavities 206 provide flexibility to the core member 200.

Figure 10:
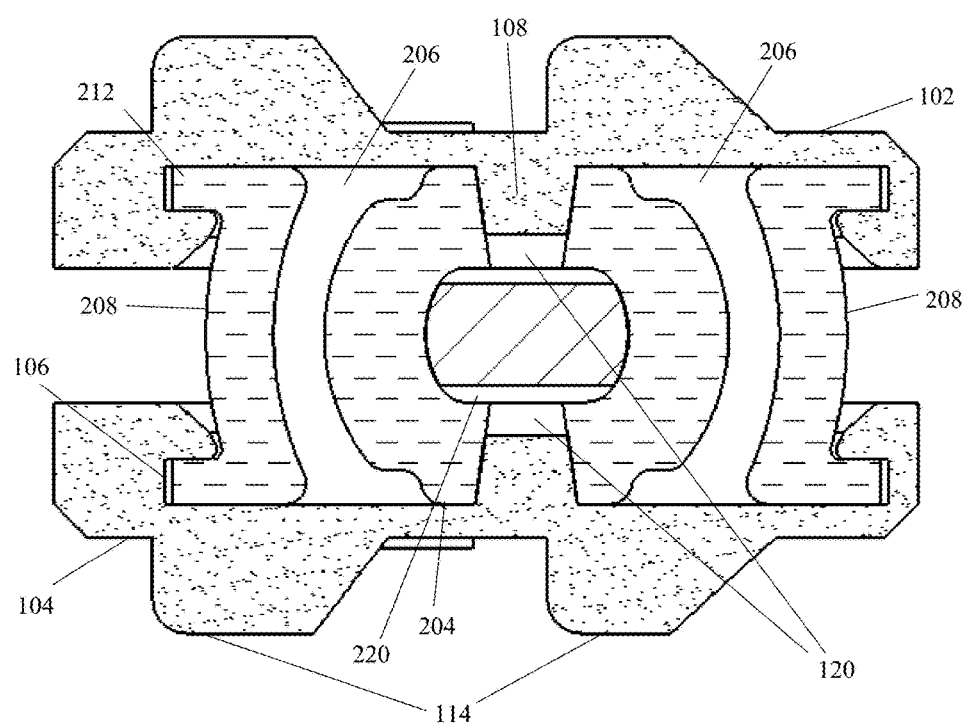
FIG. 10 is a cross-sectional side view of the artificial intervertebral disc of FIG. 1.

Referring to FIGS. 9 and 10, the outer wall 208 is formed radially outward from the outer cavities 206. The outer wall 208 may be thicker on one side to limit compression on a particular side. The core member 200 has radial extensions 212 at its upper and a lower ends 230, 232, which extend radially outwardly from the outer wall 208. As it will be described in more detail below, the radial extensions 212 are sized and shaped according to grooves 106 of the upper and lower base members 102, 104 such that a snug engagement is formed therebetween. The core member 200 also includes radial extension notches or indents 216 at opposing sides on each radial extension 212, as shown for example in FIGS. 5 and 6.

Referring to FIGS. 5-7 and 9, in the exemplar embodiments, radial wall protrusions 214 extend axially from the radial walls 210 on the upper and lower ends 230, 232 of the core member 200. As it will be described in more detail below, the radial wall protrusions 214 function as locking members. As well, the radial wall protrusions 214 have excellent wear and fatigue resistance.

It is preferred that the core member 200 be made of a biocompatible elastic material such as thermoplastic elastomers, polyether ether ketone, silicone, and rubber. These materials are chosen not only due to their elasticity but also because it is preferred that the materials are less likely creating artifacts in medical images.

Figure 11:
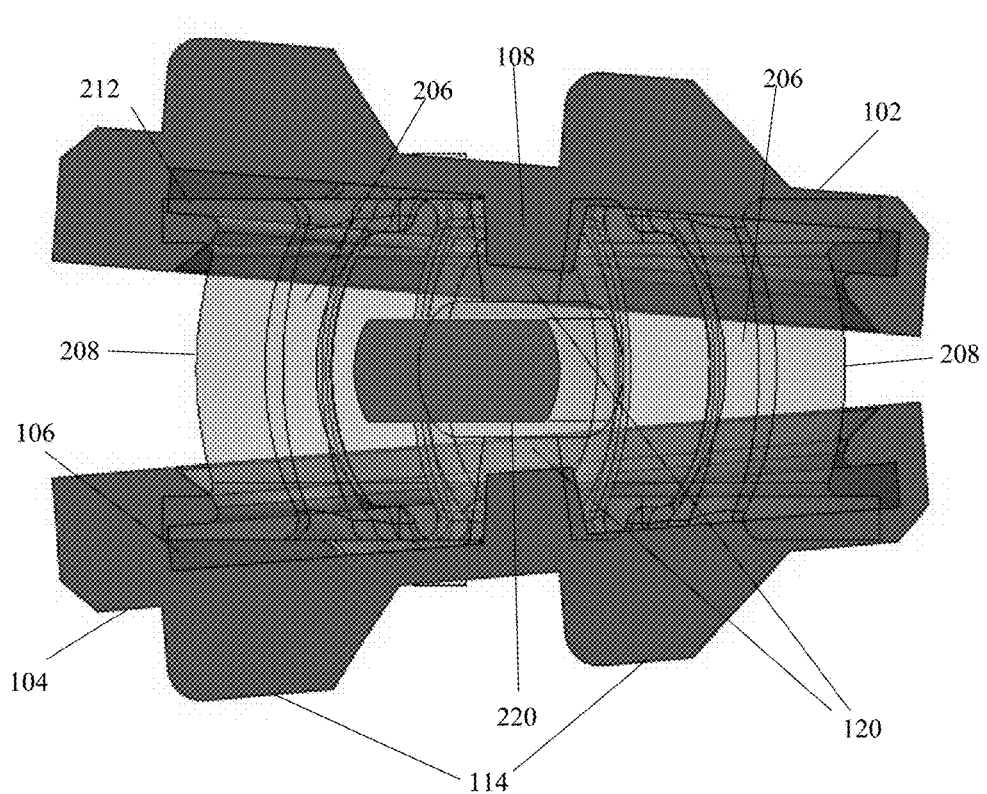
FIG. 11 is another two cross-sectional side views of the artificial intervertebral disc of FIG. 1 superimposed with each other.

Referring to FIGS. 10 and 11, a core spacer 220 is positioned within the intermediate section 202b of the inner cavity 202. As mentioned above, in the exemplar embodiments, the inner cavity 202 has a larger diameter at its center 202b to accommodate the core spacer 220. It is preferred that the core spacer 220 fits snugly within the intermediate section 202b to ensure that the core spacer 220 remain at the center of the inner cavity 202 within the intermediate section 202b. In this configuration, additional axially stability is provided to the overall structure 100. As shown in FIG. 11, the core spacer 220 serves as a guide to determine the positioning of the base members 102, 104, namely, the angle formed between the same.

It is preferred that the core spacer 220 is made of a biocompatible radio-opaque material, such as titanium, cobalt-chromium, bioceramics, stainless steel, and nickel titanium. Radio-opaque materials such as the aforementioned are preferred because displacement of the core spacer 220 must be detectable by x-ray to analyze proper size and fit of the disc 100.

Figure 5:
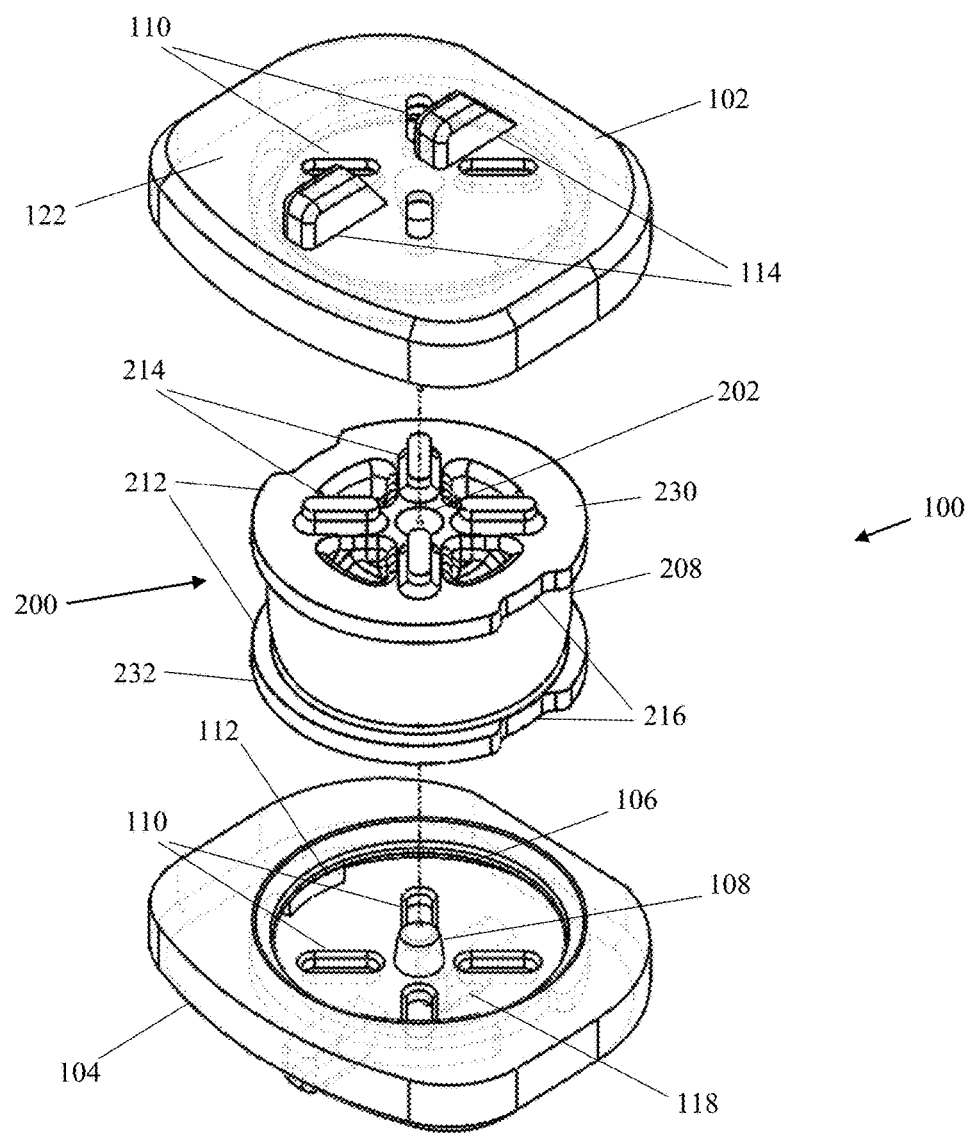
FIG. 5 is an exploded view of the artificial intervertebral disc of FIG. 1 with three-dimensional views superimposed therewithin.
Figure 6:
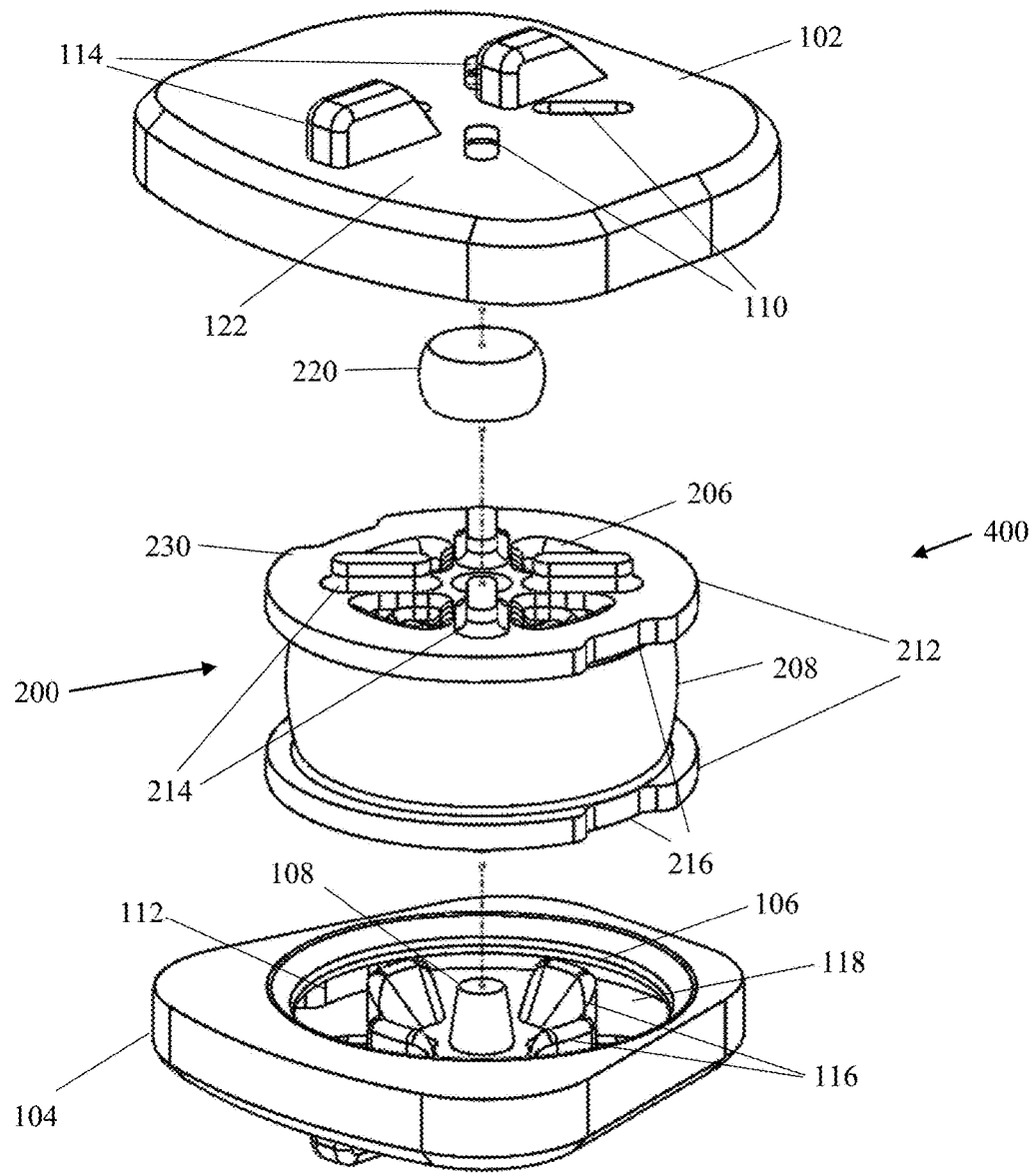
FIG. 6 is an exploded view of another embodiment of an artificial intervertebral disc of the present invention.
Figure 7:
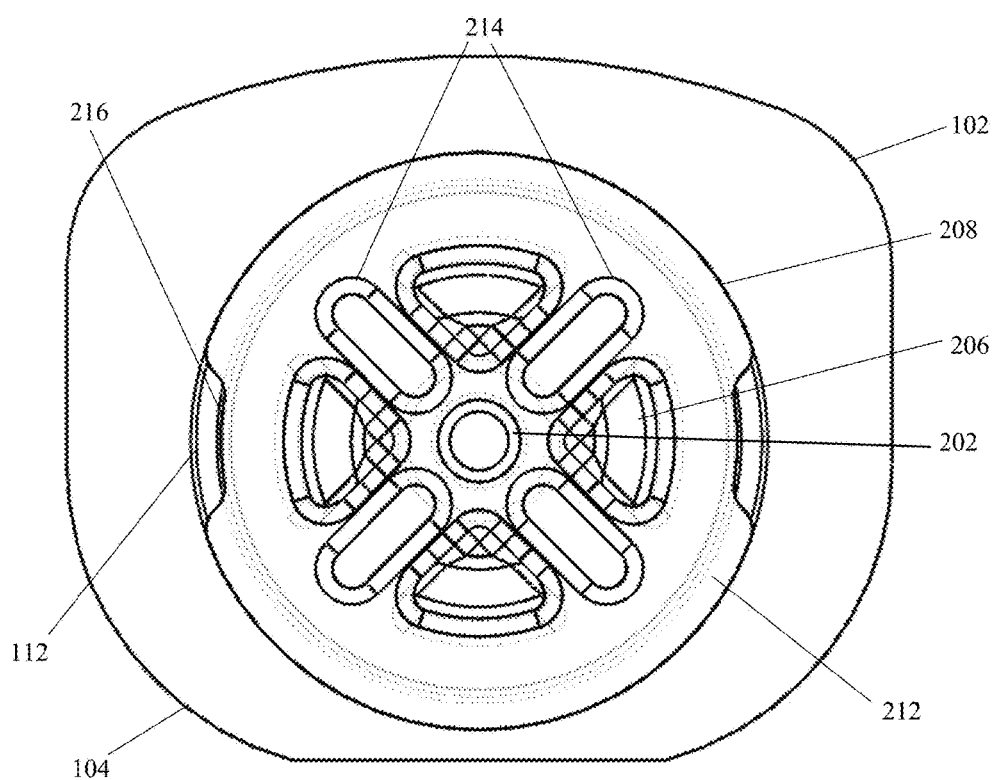
FIG. 7 is a top view of the embodiments of the artificial intervertebral discs of the present invention without the top base member with a cross-sectional view superimposed therewithin.
Figure 8:
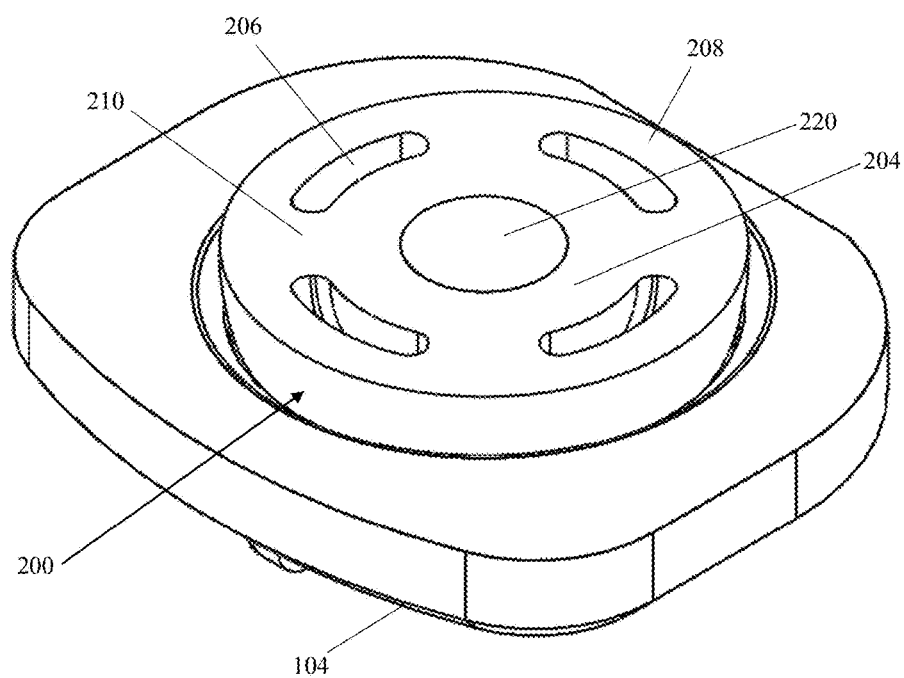
FIG. 8 is a cross-sectional perspective view of the embodiments of the artificial intervertebral disc of the present invention.

Referring to FIGS. 1-6, 10 and 11, the upper and lower base members 102, 104 are substantially identical to each other and oppose each other in mirror image. The inner surfaces 118 of the upper and lower base members 102, 104 include indents or grooves 106 circumscribing an inner section thereof. As mentioned above, the grooves 106 are sized and shaped to match the radial extensions 212 of the core member 200, as shown in FIG. 10. As shown in FIGS. 5 and 6, the upper and lower base members 102, 104 also include groove tabs 112 extending from the inner section of the base members 102, 104, which are sized and shaped to match the radial extension notches 216 or the core member 200.

Base markers 108 extend inwardly from an inner surface of each upper and lower base member 102, 104 from a substantial center of the same. Each base marker 108 is sized and shaped to engage the upper and lower sections of the inner cavity 202a, 202c in form fit, as shown in FIG. 10. Similar to the core spacer 220, it is preferred that the base markers 108 are made of a biocompatible radio-opaque material, such as titanium, cobalt-chromium, bioceramics, stainless steel, and nickel titanium. Radio-opaque materials such as the aforementioned are preferred because displacement of the base markers 108 must be detectable by x-ray to analyze proper fit of the disc 100.

Referring to FIG. 6, in another embodiment 400, optionally, inner surfaces of the upper and lower base members 102, 104 include supplementary protrusions 116. The supplementary protrusions 116 are sized and shaped to engage with upper and lower sections of the outer cavities 206. Thus, an additional locking means is provided.

Figure 14:
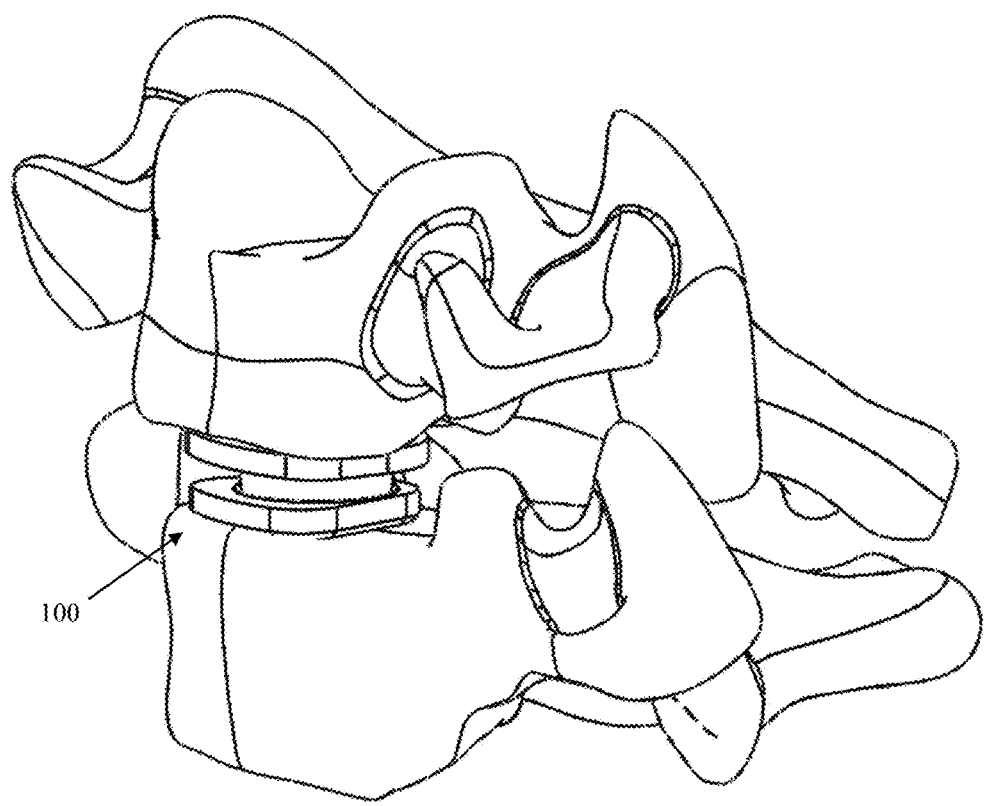
FIG. 14 is a side perspective view of a human spine with the artificial intervertebral disc of FIG. 1 installed anteriorly therein.
Figure 15:
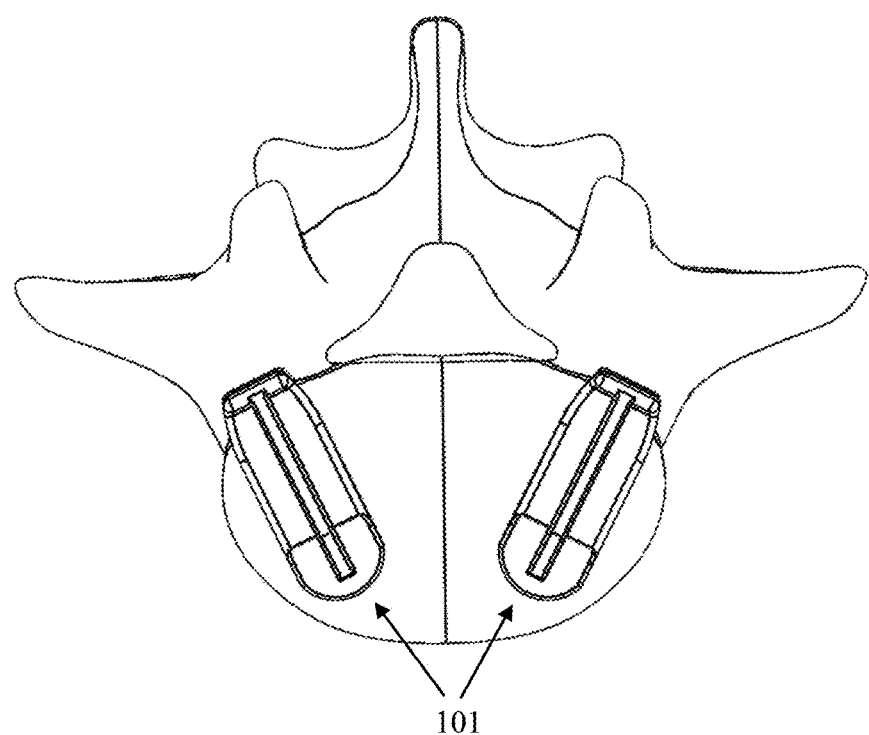
FIG. 15 is a top view of a human spine with the artificial intervertebral disc of FIGS. 12 and 13 installed posteriorly therein.

Referring to FIGS. 1-6, the outer surfaces 122 of the upper and lower base members 102, 104 include stabilizing protrusions 114 to aid in stabilizing the disc 100 between the vertebral members, as shown for example in FIGS. 14 and 15. The stabilizing protrusions 114 not only provide sufficient friction with the spine to form a stable engagement, but also fuses with the spine for a more permanent engagement. One of ordinary skill in the art will recognize that the stabilizing protrusions 114 could take on various shapes and sizes without departing from the spirit and scope of the present invention.

The upper and lower base members 102, 104 are made of a biocompatible material such as titanium, cobalt-chromium, bioceramics, stainless steel, nickel titanium, polyether ether ketone (PEEK), or other radio-opaque polymers visible by x-ray.

Figure 12:
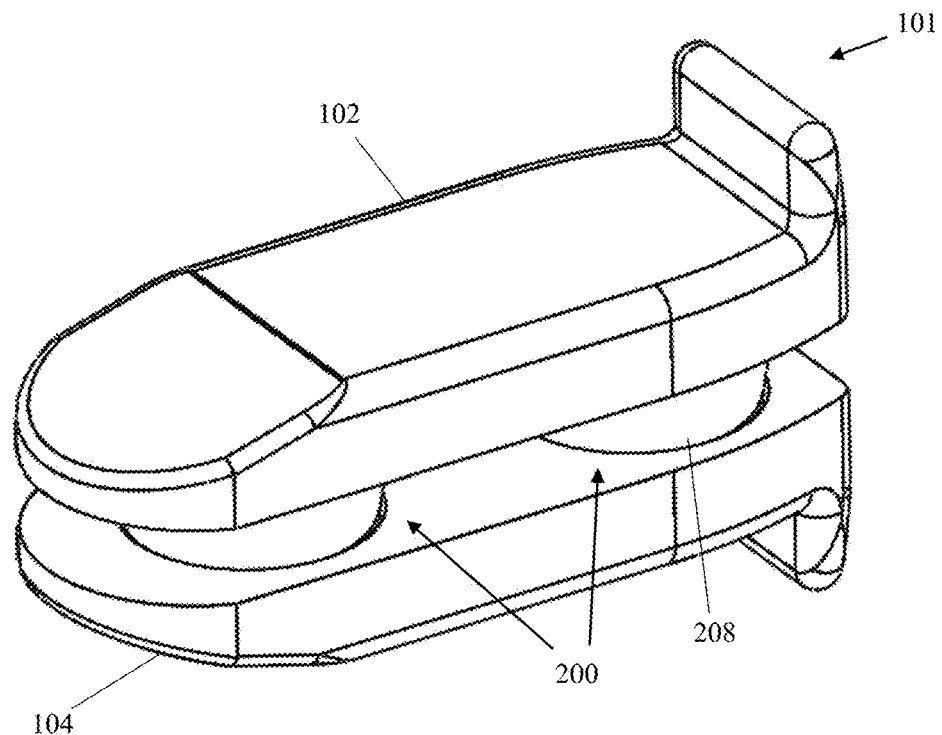
FIG. 12 is a perspective view of another embodiment of an artificial intervertebral disc of the present invention.
Figure 13:
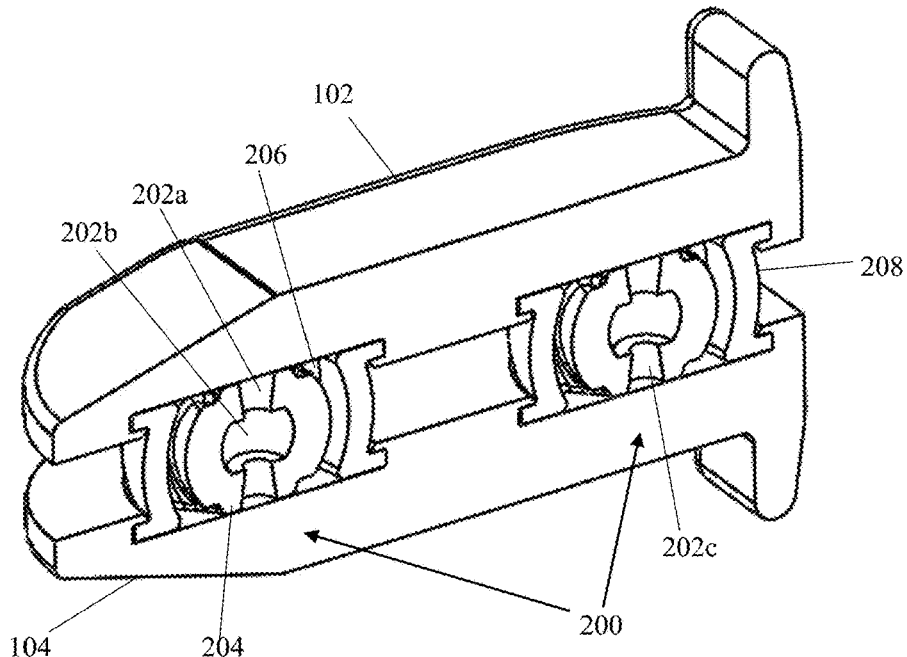
FIG. 13 is a cross-sectional view of the artificial intervertebral disc of FIG. 12.

FIGS. 12-13 show an alternative embodiment 101 comprising narrow upper and lower base members 102, 104 and two smaller core members 200. This embodiment can be used for posterior surgical approaches where narrower discs are required to avoid nerves during implantation.

Referring to FIGS. 5, 10 and 11, in operation, the core member 200 is operably coupled to the upper and lower base members 102, 104 by engagement of the radial extensions 212 and the grooves 106. The base markers 108 are inserted into the inner cavity 206, leaving a gap 120 between the base markers 108 and the core spacer 220, as shown in FIG. 10. That is, rotation of the core member 200 is constrained by means of locking mechanisms comprising protrusions 214 or indentations 202, 216 on the core member 200 coupled to corresponding indentations 110 or protrusions 108, 112 on the upper and lower base members 102, 104. Specifically, the radial walls 210 extending to form radial wall protrusions 214 on the upper and lower ends 230, 232 of the core member 200 are coupled to base indentations 110 on the inner surfaces 118 of the upper and lower base members 102, 104. The radial extension notches 216 on the radial extensions 212 of the core member 200 are coupled to groove tabs 112 on the grooves 106 of the upper and lower base members 102, 104.

Referring to FIG. 11, when one side of the intervertebral disc 100 is compressed, the inner and outer walls 204, 208 on that side compress in height and expand in width, displacing the core spacer 220 horizontally in the opposing direction. The elastic core member 200 allows for movement with low friction and provides wear-resistance and shock-absorption. The inner and outer cavities 202, 204 allow for more flex in the inner and outer walls 204, 208 and therefore, more shock absorption and a greater range of motion including translational and torsional motion, while still providing support and tension. The core spacer 220 can be displaced within the inner cavity 202 by the compression of the inner wall 204 between the upper and lower base members 102, 104, resulting in perpendicular expansion. The displacement can be observed by x-ray during or after implantation. The size of the gap 120 between the core spacer 220 and the upper and lower base members 102, 104 or base markers 108 can be used to determine the degree of compression at rest. Excessive resting compression can be remedied by using an intervertebral disc 100 of reduced height.

Referring to FIG. 14, the primarily embodiment, shown in FIGS. 5 and 6, is intended for anterior insertion between two adjacent vertebral bodies, for example, between the L5 vertebral body and S1 sacrum. The disc 100 could be manufactured with a height of 5-14 millimeters for installation in the cervical and thoracic regions and 7-16 millimeters for installation in the lumbar region.

Referring to FIG. 15, in the alternative embodiment 101 shown in FIGS. 12 and 13, intended for use in posterior surgical approaches, dimensions are 10-12 mm wide, 25-40 mm in length and 7-16 mm in height due to the need to avoid nerves during insertion. The anterior embodiment 101 comprises multiple core members 200 between the long narrow upper and lower base members 102, 104.

Figure 16:
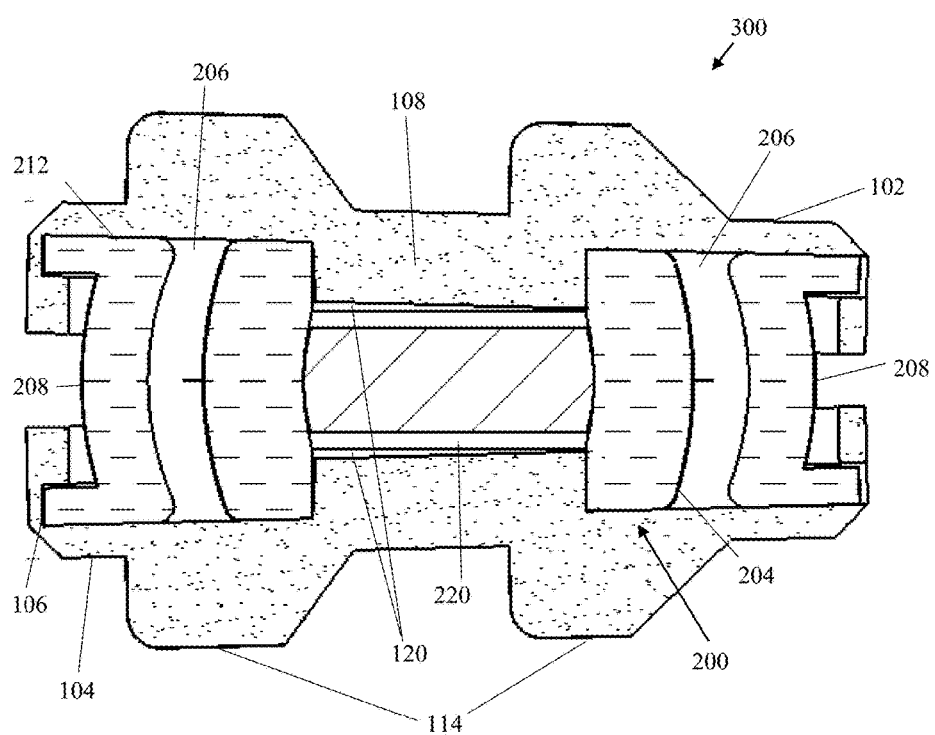
FIG. 16 is a cross-sectional side view of another embodiment of the artificial intervertebral disc of the present invention.

Referring to FIG. 16, in another alternative embodiment 300 of the intervertebral implant of the present invention, the core member 200 is manufactured such that one side has a lower height than the opposing side at a rested state. That is, the implant 300 is preconfigured to conform to the natural lordotic curvature of a patient's spine to ensure a more accurate and comfortable fit. Multiple implants with varying lordotic angles could be manufactured. In one possible application, during the medical procedure, the disc of the first embodiment 100 as shown in FIG. 10 can be inserted as a test to determine the lordosis by x-ray. Then the disc of the first embodiment 100 can be removed and a disc with a matching lordosis angle 300 can be permanently inserted.

In addition, in the embodiment 300 shown in FIG. 16, the inner cavity 120 is wider to more easily accommodate the core spacer 220 during manufacture. This wider inner cavity 120 can be utilized in the other embodiments as well.

Figure 17:
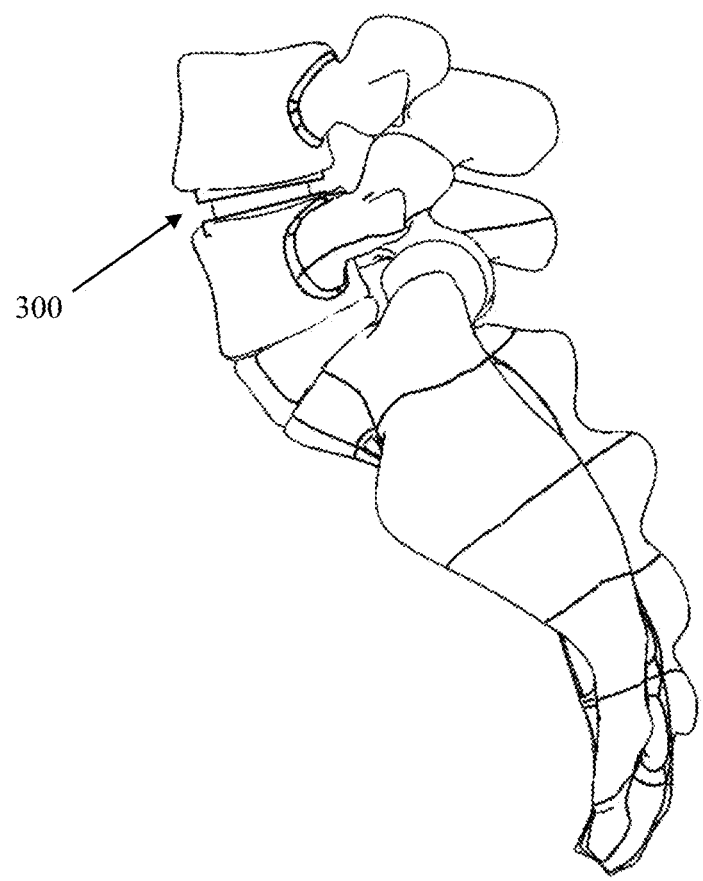
FIG. 17 is a side perspective view of a human thoracolumbar spine with the artificial intervertebral disc of FIG. 16 installed anteriorly therein.

Referring to FIG. 17, the alternative embodiment 300 of FIG. 16 is shown after insertion. As shown in the figure, a natural lordosis is accommodated by the disc implant 300 which has a structure corresponding to the natural lordosis.

The present invention provides an artificial disc with minimal components and no additional tools or fasteners to couple the base members to the core member. In addition, the artificial disc of the present invention provides six degrees of freedom and supports translational motion, i.e., upper and lower base members are capable of moving in different lateral directions, torsional motion, as well as axial compression.

As seen above, the artificial disc of the present invention is particularly useful for surgeons during trialing, i.e., testing of the artificial disc for proper size, prior to installing permanently. The artificial disc of the present invention is also useful for determining performance of the disc after installation. The radio-opaque base members and core spacer allow the physician to view the positioning of the disc by x-ray, including displacement of the components of the disc. More specifically, x-rays are examined during testing to determine the lordotic angle formed between the base members. In addition, lordosis is observed by determining displacement distance of the core spacer. Thus, the artificial disc of the present invention is highly effective in properly sizing the implant.

The present invention may be embodied in other specific forms without departing from its spirit or essential characteristics. The described embodiments are to be considered in all respects only as illustrative and not restrictive. The scope of the invention will be, therefore, indicated by claims rather than by the foregoing description. All changes, which come within the meaning and range of equivalency of the claims, are to be embraced within their scope.

The invention claimed is:

1. An intervertebral implant comprising:
a substantially cylindrical core member having an upper end and an axially opposing lower end, the core member comprising:
an inner cavity extending axially between a center of the upper end and a center of the lower end, and
at least one outer cavity extending axially between the first upper and the lower end, and radially between the inner cavity and a radially outer surface of the core member,
a core member inner wall formed between the inner cavity and the at least one outer cavity,
a core member outer wall formed between the at least one outer cavity and the outer surface of the core member, the core member outer wall having an upper radial extension positioned on the upper end of core member, a lower radial extension positioned on the lower end of the core member, and an axial extension positioned therebetween, and
at least one first locking member positioned on at least one of the core member upper end and the core member lower end;
a core spacer positioned within the inner cavity;
an upper base member positioned on the upper end of the core member, the upper base member having an upper retaining wall positioned on a periphery thereof, the upper retaining wall having an upper groove positioned on an inner portion thereof;
a lower base member positioned on the lower end of the core member, the lower base member having a lower retaining wall positioned on a periphery thereof, the lower retaining wall having a lower groove positioned on an inner portion thereof; and
at least one second locking member positioned on an inner surface of at least one of the upper base member and the lower base member;
wherein the upper and lower base members are operably coupled with the core member by engagement of the upper radial extension and the upper groove, and the lower radial extension and the lower groove, and by engagement of the at least one first locking member and the at least one second locking member; and
wherein the core member is constructed of an elastic material such that inner walls are displaceable toward the outer cavity.

2. An intervertebral implant comprising:
a substantially cylindrical core member having an upper end and an opposing lower end, the core member comprising:
an inner cavity extending axially between a center of the upper end and a center of the lower end, and
at least one outer cavity extending axially between the upper end and the lower end, and radially between the inner cavity and an outer surface of the core member,
a core member inner wall formed between the inner cavity and the at least one outer cavity, and
a core member outer wall formed between the at least one outer cavity and the outer surface of the core member, the core member outer wall having an upper radial extension positioned on the upper end of core member, a lower radial extension positioned on the lower end of the core member, and an axial extension positioned therebetween;
a core spacer positioned within the inner cavity;
an upper base member positioned on the upper end of the core member, the upper base member having an upper retaining wall positioned on a periphery thereof, the upper retaining wall having an upper groove positioned on an inner portion thereof;
a lower base member positioned on the lower end of the core member, the lower base member having a lower retaining wall positioned on a periphery thereof, the lower retaining wall having a lower groove positioned on an inner portion thereof;
wherein the upper and lower base members are operably coupled with the core member by engagement of the upper radial extension and the upper groove, and the lower radial extension and the lower groove.

3. The intervertebral implant of claim 2, wherein the inner cavity extends completely through the core member.

4. The intervertebral implant of claim 2, wherein the outer cavity extends completely through the core member.

5. The intervertebral implant of claim 2, further comprising at least one first locking member positioned on at least one of the core member upper end and the core member lower end.

6. The intervertebral implant of claim 5, further comprising at least one second locking member positioned on an inner surface of at least one of the upper base member and the lower base member.

7. The intervertebral implant of claim 6, wherein the at least one first locking member engages the at least one second locking member.

8. The intervertebral implant of claim 7, wherein the at least one first locking member is a protrusion extending from the at least one of the core member upper end and the core member lower end, and the at least one second locking member is an indentation extending into the inner surface of at least one of the upper base member and the lower base member.

9. The intervertebral implant of claim 7, wherein the at least one first locking member is an indentation extending into the at least one of the core member upper end and the core member lower end, and the at least one second locking member is a protrusion extending from the inner surface of at least one of the upper base member and the lower base member.

10. The intervertebral implant of claim 9, wherein the indentation is the inner cavity.

11. The intervertebral implant of claim 2, wherein the core member is constructed of an elastic material such that inner walls are displaceable toward the outer cavity.

12. The intervertebral implant of claim 2, wherein the core spacer is constructed of a radio opaque material.

13. The intervertebral implant of claim 2, wherein at least one of the upper and lower base members is constructed of a radio opaque material.

14. An intervertebral implant comprising:
a core member having an upper end and an opposing lower end, the core member comprising:
an inner cavity extending axially between a center of the upper end and a center of the lower end, and
at least one outer cavity extending axially between the upper end and the lower end, and radially between the inner cavity and an outer surface of the core member,
a core member inner wall formed between the inner cavity and the at least one outer cavity, and
a core member outer wall formed between the at least one outer cavity and the outer surface of the core member;

at least one first locking member positioned on at least one of the core member upper end and the core member lower end; and a core spacer positioned within the inner cavity;

an upper base member positioned on the upper end of the core member;

a lower base member positioned on the lower end of the core member; and at least one second locking member positioned on an inner surface of at least one of the upper base member and the lower base member;

wherein the at least one first locking member engages the at least one second locking member.

15. The intervertebral implant of claim 14, wherein the at least one first locking member is an indentation extending into the at least one of the core member upper end and the core member lower end, and the at least one second locking member is a protrusion extending from the inner surface of at least one of the upper base member and the lower base member.

16. The intervertebral implant of claim 15, wherein the indentation is the outer cavity.

17. The intervertebral implant of claim 14, wherein the core spacer, upper base and lower base are constructed of a radio-opaque material.

18. An intervertebral implant comprising:
a core member having an upper end and an opposing lower end, the core member comprising:
an inner cavity extending axially between a center of the upper end and a center of the lower end, and
at least one outer cavity extending axially between the upper end and the lower end, and radially between the inner cavity and an outer surface of the core member,
a core member inner wall formed between the inner cavity and the at least one outer cavity, and
a core member outer wall formed between the at least one outer cavity and the outer surface of the core member;
at least one first locking member positioned on at least one of the core member upper end and the core member lower end; and
a core spacer positioned within the inner cavity;
wherein the outer cavity extends completely through the core member.

19. The intervertebral implant of claim 18, wherein a radial distance between the core member inner and outer walls is greater on the upper and lower ends than a radial distance between the core member inner and outer walls intermediate the upper and lower ends.

\* \* \* \* \*